United States Patent [19]
Wilf

[11] Patent Number: 5,905,197
[45] Date of Patent: May 18, 1999

[54] MEMBRANE SAMPLING DEVICE

[75] Inventor: Mark Wilf, San Diego, Calif.

[73] Assignee: Hydranautics, Inc., Oceanside, Calif.

[21] Appl. No.: 09/010,900

[22] Filed: Jan. 22, 1998

[51] Int. Cl.[6] .................................................. G01N 1/00
[52] U.S. Cl. ....................................................... 73/86; 73/38
[58] Field of Search ........................... 73/38, 86, 863.21, 73/863.23, 863.25, 865.9; 55/520; 210/85, 285, 348, 497.1

[56] References Cited

U.S. PATENT DOCUMENTS

| | | |
|---|---|---|
| 3,759,087 | 9/1973 | Iwao et al. . |
| 3,782,175 | 1/1974 | Roman . |
| 4,128,004 | 12/1978 | Caron et al. . |
| 4,207,870 | 6/1980 | Eldridge . |
| 4,256,120 | 3/1981 | Finley . |
| 4,384,474 | 5/1983 | Kowalski . |
| 4,515,007 | 5/1985 | Herman . |
| 4,676,092 | 6/1987 | Tuttle . |
| 4,679,571 | 7/1987 | Frankel et al. . |
| 4,704,899 | 11/1987 | Burr et al. . |
| 4,881,176 | 11/1989 | Kononov . |
| 4,888,977 | 12/1989 | Chehab et al. . |
| 4,890,484 | 1/1990 | Telfer et al. . |
| 5,101,671 | 4/1992 | Elgas . |
| 5,125,277 | 6/1992 | Zievers ............................... 73/863.23 |
| 5,417,101 | 5/1995 | Weich . |
| 5,448,922 | 9/1995 | Kimbell et al. ...................... 73/863.23 |
| 5,460,733 | 10/1995 | Rasmussen et al. . |
| 5,543,007 | 8/1996 | Takagaki et al. . |
| 5,777,241 | 7/1998 | Evenson ............................... 73/863.25 |

*Primary Examiner*—Robert Raevis
*Attorney, Agent, or Firm*—McDermott, Will & Emery

[57] ABSTRACT

A membrane sampling device for use in a membrane filtration system having one or more pressure vessels for determining whether a filter membrane elements are performing properly or need replacement. The membrane sampling device is adapted to test operating conditions and to provide performance indicia in RO/UF systems without removal of filter membrane elements from the pressure vessel. A testing system is also provided that provides an improved means for testing multiple membrane sampling devices.

25 Claims, 3 Drawing Sheets

MEMBRANE SAMPLING DEVICE

BACKGROUND OF THE INVENTION

1. Field of the Invention

The present invention relates generally to membrane filtration systems and in particular to a membrane sampling device that provides indicia concerning the performance of the membrane and the operating conditions in a pressure vessel used in ultrafiltration (UF) or reverse osmosis (RO) systems.

2. Discussion of the Prior Art

Conventional membrane filtration systems can be used in various fields for applications to filter soluble salts or suspended particles from a feed liquid, for example, RO applications in filtering seawater or brackish water. Such membrane filtration systems typically use a pressure vessel to house one or more membrane elements that filter the feed liquid. Conventional membrane elements are typically manufactured in diameters ranging from approximately four to eight inches and in lengths of forty to sixty inches and, as a result, each membrane element can have approximately four hundred square feet of membrane area. Multiple pressure vessels can be configured in groups or concentrate stages, whereby the concentrate from the first stage is supplied to the feed of the second stage and so on for other concentrate stages. The parameters of flow and pressure in the pressure vessel are controlled with feed and concentrate valves, whereby the feed valve is disposed after a high pressure pump to control the flow of feed to the pressure vessels of the concentrate stage and the concentrate valve is disposed at the outlet of the concentrate stage to control the feed pressure thereto. In this manner, each concentrate stage filters the soluble salts or suspended particles from the feed liquid.

Membrane filtration systems can have problems of compaction and fouling that diminish the performance of such systems. For example, membrane material exposed to a feed flow at high pressure or high temperature will increase the density of the membrane material, which is referred to as compaction. Such compaction lowers membrane performance by decreasing the flux or rate of diffusion of water and dissolved constituents through the membrane material, whereby higher feed pressure has to be applied to maintain a desired permeate flow. Compaction also lowers salt diffusion through the membrane material, thereby resulting in lower permeate salinity.

In addition, membrane fouling has a negative effect on membrane performance and, in extreme cases, may result in non-reversible membrane degradation. Membrane fouling is caused by deposits of inorganic or organic substances on the membrane surface and/or blockage of the feed channels formed in the membrane elements. In the initial stages of membrane fouling, a decrease in the system performance is characterized by an increase in the pressure drop across the membrane filtration system. If such membrane fouling continues uncontrolled, membrane performance will continue to decrease until the performance of the system falls below a useful level for a given application, whereby membrane elements have to be replaced at such point. Conventional tests to determine the nature and extent of fouling require that a sample of the membrane element be taken and analyzed in order to evaluate the condition of the membrane element and to characterize the membrane surface. Such tests require opening the pressure vessel to remove and take samples of the membrane elements, thereby stopping the normal operation of the membrane filtration system. Membrane fouling problems are particularly costly in membrane filtration systems that pack one or more membrane elements into a particular pressure vessel because extensive time is required to initially pack and then unpack such membrane elements from the affected pressure vessels.

Conventional membrane filtration systems have not addressed the above-identified problems and such problems are not remedied in the prior art. Both compaction and fouling problems are characterized by a need to increase feed pressure to produce design permeate flow. Fouling by suspended particles also may result in increase of pressure drop in the system. Determining the condition of membrane elements requires removal so as to conduct a desired test and, additionally, such tests may require the use of dedicated equipment or a particular kind of testing facility. If the desired test has to be conducted at a special testing facility, replacement membrane elements are required for continued system use, thereby increasing the cost, labor expended, and downtime of the system. For the purpose of identifying membrane fouling and providing an effective remedy, it is important to obtain information on performance of individual membrane elements. Such information is not available in the current membrane filtration systems.

The membrane sampling device of the present invention seeks to overcome these and other shortcomings of the prior art so as to obtain information on the performance of the membrane filtration system in an effective and convenient way.

SUMMARY OF THE INVENTION

Accordingly, an object of the present invention is to provide an improved method and apparatus for determining indicia of performance of a membrane element at the site of use. Information on the condition of the membrane element is advantageous, for example, to assess the degradation of the membrane element, to estimate the degree of fouling of the surface of the membrane element, and to identify the nature and source of the foulant so as to determine an effective membrane cleaning solution or procedure.

Another object of the present invention is to provide a membrane sampling device that provides real-time performance indicia representative of the operating conditions in a pressure vessel having multiple membrane elements disposed therein. The membrane sampling device of the present invention provides real-time performance indicia of the nature and degree of foulant of membrane elements within a pressure vessel.

Still another object of the present invention is to provide a membrane sampling device that allows for the collection of performance indicia representative of the flux and conductivity of the feed, concentrate and permeate fluids in the membrane filtration system. Such membrane sampling device has advantages of providing performance indicia in real-time such as during the operation of the membrane filtration system, or performance indicia with minimal interruption of the operation of the membrane filtration system.

Another object of the present invention is to provide a cell-test membrane that gives the performance indicia of the nature and degree of fouling of the membrane element and surface thereof. Such cell-test membrane is small and compact and provides unique advantages in the storage of the cell-test membrane for various purposes or for shipment of the cell-test membrane to testing facilities.

Yet another object of the present invention is to provide an end plate having a separate aperture for the membrane sampling device. Such aperture provides a simple means to insert and remove the membrane sampling device from the pressure vessel so as to allow for the collection of performance indicia respective of the flux and conductivity of the feed, concentrate and permeate fluids in the membrane filtration system. Such aperture also allows for the real-time testing of the conditions and performance indicia regarding the degree of fouling of the membrane elements in the pressure vessel using the cell-test membrane. Such cell-test membrane provides performance indicia without the need to pack and unpack the membrane elements from the system. Such aperture has advantages over prior devices that include minimizing the cost, down-time and conditions necessary to determine performance indicia of a particular membrane filtration system.

Accordingly, the membrane sampling device of the present invention provides performance indicia of a membrane filtration system. The device comprises a plug that includes an opening and the plug is adapted to be disposed in an aperture of an end plate configured to seal an open end of a pressure vessel. The membrane filtration system supplies and collects fluids from the pressure vessel, for example, the system includes a permeate port for collecting permeate fluid, a feed port for supplying a flow of feed fluid and a concentrate port for collecting a flow of concentrate fluid. The permeate port can be located in the end plate. The feed and concentrate ports can be located in the wall (at opposite ends) of the pressure vessel or, alternatively, in the end plate to supply or receive feed or concentrate fluids, respectively. A tube can be received by the opening of the plug. A cell-test membrane is disposed on the tube and the cell-test membrane includes an envelope formed of a membrane material and a spacer material, whereby the envelope and spacer material are spirally-wound to form such cell-test membrane. The membrane sampling device can gather performance indicia that include the nature and degree of foulant in the membrane filtration system, the permeate flow rate, and the composition of the permeate collected from the cell-test membrane. Alternatively, a pipe can be received in the opening and the pipe can receive the tube. The pipe is configured with an outer dimension less than an inner dimension of the tube so as to be received by the tube. The plug includes a closing cup for sealing the opening or pipe during operation of the pressure vessel, whereby the closing cup is adapted to withstand the operating pressure of the pressure vessel. The envelope can be formed from, for example, a rectangle of a membrane material folded at a midpoint thereof. The envelope is usually formed from the same material as is used to make the membrane of the filtration system. The folded membrane material is affixed at the free edges to form the envelope and then rolled with the spacer material to form a cylindrical cell-test membrane with the tube extending therefrom.

Accordingly, the membrane sampling device of the present invention provides an end plate for use in a pressure vessel of a membrane filtration system. The end plate is configured to seal an open end of a pressure vessel. The end plate includes an aperture formed in the end plate and a membrane sampling device adapted to be received in the aperture. A permeate port can be located in the end plate to collect permeate fluids. Feed and concentrate ports can be located in the wall (at opposite ends) of the pressure vessel or, alternatively, in the end plate to supply or receive feed or concentrate fluids. The membrane sampling device is configured to provide performance indicia of a membrane element disposed in the pressure vessel and other conditions of the membrane filtration system. The membrane sampling device includes a plug having an opening disposed along the center thereof, the plug being configured with an outer dimension less than an inner dimension of said aperture so as to be received by the aperture. The membrane sampling device may include a closing cup for sealing the opening during the operation of the pressure vessel, whereby the closing cup is adapted to withstand the operating pressure of the pressure vessel. The cell-test membrane is disposed on a tube and such cell-test membrane can be formed from an envelope of a membrane material that encloses a spacer material. The tube is received by the opening of the plug. Alternatively, a pipe can be disposed in the opening and adapted to receive the tube so as advantageously to be detachable from the pipe for ease of replacement, to reduce waste, and to reduce manufacturing and labor costs. The envelope and spacer material is spirally-wound to form a cell-test membrane. The cell-test membrane is located in the pressure vessel for effective sampling of performance indicia of the membrane and/or of the membrane filtration system.

BRIEF DESCRIPTION OF THE DRAWINGS

The features and advantages of the present invention will become more clearly appreciated from the following description taken in conjunction with the accompanying drawings in which like elements are denoted by like reference numerals and in which.

DETAILED DESCRIPTION OF THE PREFERRED EMBODIMENTS

Figure 1:
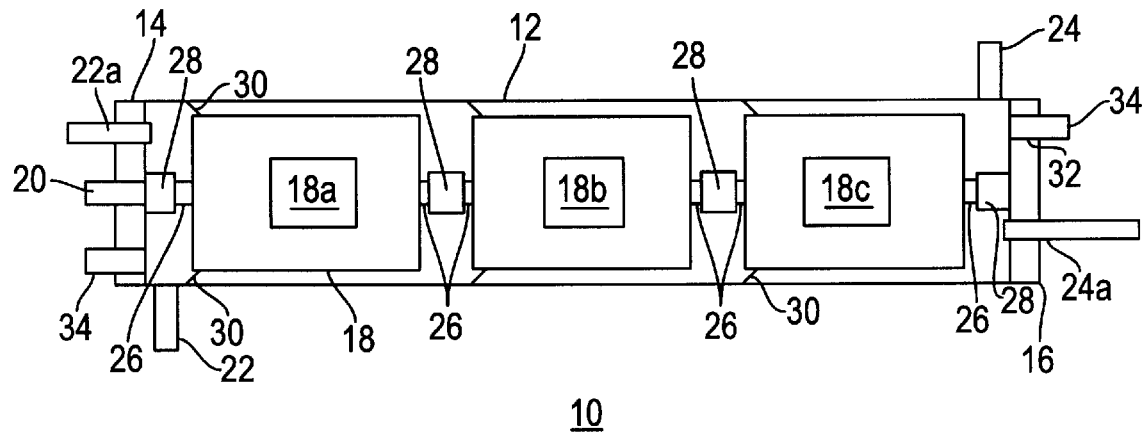
FIG. 1 is a schematic diagram illustrating a membrane sampling device in a pressure vessel of a membrane filtration system.

As illustrated in FIG. 1, the present invention is described in relation to an RO or UF membrane filtration system 10 that is configured to include a pressure vessel assembly 12 of a long cylindrical shape having open ends thereof, end plates 14 and 16 adapted to seal each open end of the pressure vessel 12, and a plurality of membrane elements 18. As described herein, the membrane filtration system 10 can be configured to include one or more pressure vessels arranged in concentrate stages. Each pressure vessel 12 in a concentrate stage includes end plates 14 and 16 to close and seal the pressure vessel such as, for example, caps or other equivalent structures. The membrane filtration system 10 supplies and collects fluids from the pressure vessel, for example, the system includes a permeate port 20 for collecting a flow of permeate fluid, a feed port for supplying a flow of feed fluid 22, and a concentrate port 24 for collecting a flow of concentrate fluid. The permeate port 20 can be located in an end plate, for example, in end plate 14. The feed and concentrate ports 22 and 24 can be located in the wall of the pressure vessel 12 at opposite ends of the pressure vessel 12. In an alternative embodiment, the end plate can be configured to have a port for either receiving the feed fluid or concentrate fluid, for example, the end plates 14 and 16 can be configured with a feed port 22a or concentrate ports 24a, respectively. In a known manner, a membrane element 18 is formed around a core tube 26 so as to allow feed fluid to flow through the feed channels formed in the membrane element 18 to conduct permeate from the pressure vessel 12. The membrane element 18 is configured to have an outer dimension less than the inner dimension of the pressure vessel 12 so that the membrane element 18 can be disposed in the pressure vessel 12. For example, each pressure vessel 12 of a particular concentrate stage may contain a plurality of membrane elements 18a, 18b and 18c connected in series by respective core tubes 26 using connectors 28.

As is shown in FIG. 1, one end of the core tube 26 of membrane element 18a is connected to the permeate port 20 of the end plate 14 and one end of core tube 26 of membrane element 18c is connected to end plate 16 so as to effectively closes off core tube 26 at the opposite end of the pressure vessel 12, thereby forcing permeate to flow from permeate port 20 of the end plate 14. The opposite ends of each of the core tubes 26 of respective membrane elements 18a and 18c are connected by connectors 28 to the intermediary membrane element 18b. A brine seal 30 is adapted to close the passage between the outside surface of the membrane element 18 and inside wall of the pressure vessel 12. The brine seal 30 is disposed on the outside of each membrane element 18a, 18b and 18c and operates to prevent feed liquid from by-passing the membrane element 18, thereby forcing the feed liquid to flow through the feed channels formed in the membrane element 18. The brine seal 30 can be an o-ring, u-packing, flange or other structure adapted to seal the passage between the outside surface of the membrane element 18 and inside wall of the pressure vessel 12. As the feed liquid flows through each subsequent membrane element, part of the feed volume is removed as permeate, which is collected by the permeate manifold (not shown). Finally, an aperture or portal 32 is provided in each of the end plates 14 and 16 and the aperture 32 is adapted to receive a membrane sampling device. In this manner, the membrane sampling device is exposed to the same operating conditions as the one or more membrane elements 18a, 18b and 18c disposed in the membrane filtration system 10.

Figure 2:
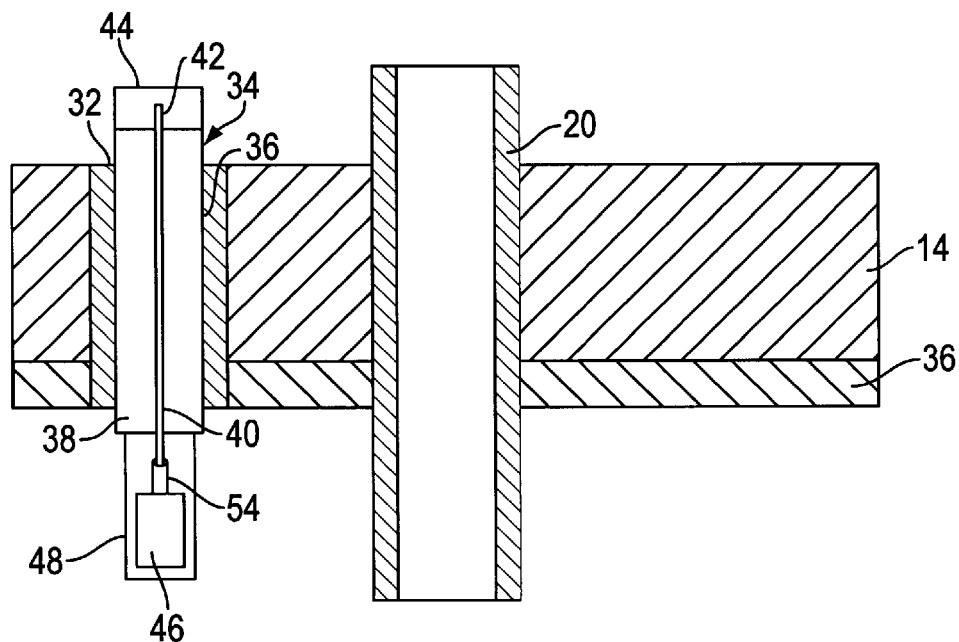
FIG. 2 is a schematic diagram illustrating a membrane sampling device in an end plate.

As is illustrated in FIG. 2, a reference numeral 34 denotes a membrane sampling device according to an embodiment of the present invention that is described, for example, in connection with the end plate 14. The end plate 14 is configured to include the aperture 32 having dimensions configured to receive the membrane sampling device 34, which advantageously can be used to provide performance indicia of conditions inside the pressure vessel and the nature and degree of fouling of the membrane elements 18a, 18b and 18c under normal operating conditions. The end plate 14 also receives the core tube 26 at the permeate port 20 to collect permeate from the membrane element 18 in a known manner. The end plate 14 can include a sealing member 36 disposed on an interior surface of the end plate 14. The aperture 32 is adapted to receive the membrane sampling device 34, for example, the membrane sampling device 34 and aperture 32 can be threaded so as to be received threadably therein. Alternatively, sealing can be achieved by means of a grooved pipe system or other equivalent structure such as a Victaulic® clamp coupling disposed in aperture 32. The Victaulic® grooved piping system is manufactured and sold by Victaulic Corporation, 4901 Kesslersville Road, Easton, Pa. 18040, and is available in many dimensions and lengths.

Figure 4:
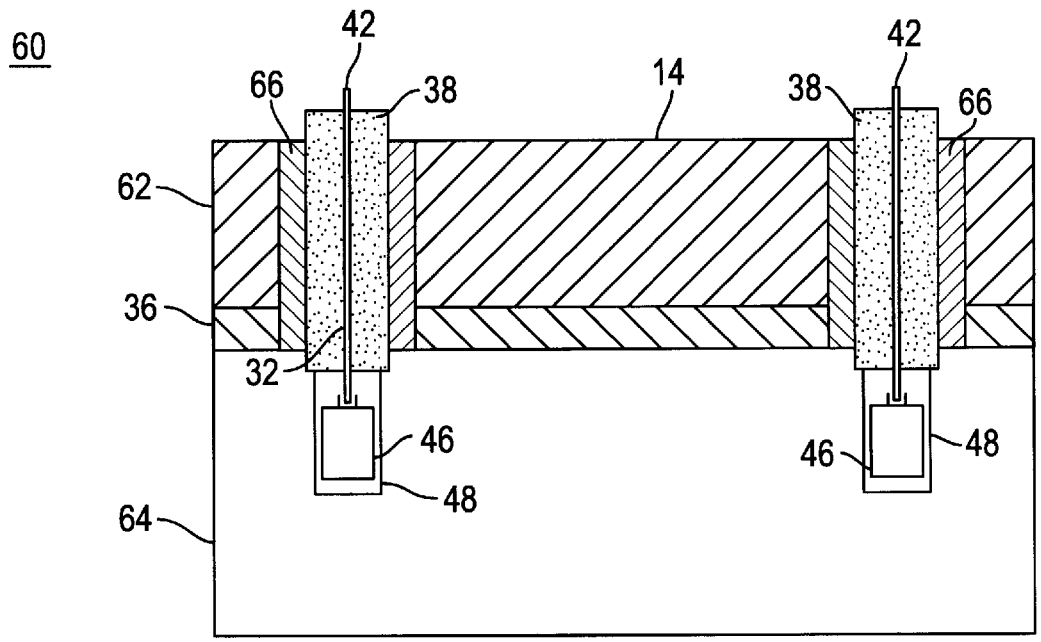
FIG. 4 is a schematic diagram of a system for testing the integrity and performance of individual membrane sampling devices.

As is illustrated in FIG. 2, the membrane sampling device 34 includes a plug 38 having an opening 40 running the axial length thereof for the collection of samples of fluid from the pressure vessel 12. The opening 40 can be located along the center of the plug 38. The plug 38 can be formed from suitable materials for RO/UF applications and that can withstand the pressure and foulant of the membrane filtration system 10. Exemplary materials for making the plug include PVC, Polypropylene, ABS or stainless steel, whereby stainless steel is the preferred material to be used herein. The opening 40 can have a pipe 42 disposed therein and the pipe 42 can be made from plastic tubing or stainless steel, whereby stainless steel exhibits the preferred qualities of resistance to water and corrosion. The plug 38 can include a closing cup or cap 44 configured to seal off the opening 40 or pipe 42 and the cap 44 is rated for the operating pressure of the pressure vessel 12. The membrane sampling device 34 further includes a cell-test membrane 46 encompassed by a permeable protective sleeve 48 as is shown in FIG. 4.

The cell-test membrane 46 can be made from any membrane material used to make commercial RO or UF membrane elements 18 such as, for example, cellulose acetate, composite aromatic polyamide, polyamide, polysulfone, polypropylene, other polyamide membrane compositions and any other suitable membrane compositions. In the preferred embodiment of the present invention, the cell-test membrane 34 can be formed from an envelope and spacer material that is spirally-wound around a tube as is described herein, however, the cell-test membrane 34 can be formed from any porous or semi-permeable material and also can be of a different construction suitable for a particular filtration application, for example, any porous or semi-permeable material formed into a plug disposed on the tube. In most applications, the membrane material of the cell-test membrane 46 will be the same or similar material of the membrane elements 18 installed in the system 10. In this manner, the membrane sampling device 10 advantageously provides representative performance indicia of the membrane elements 18 including the degree of fouling in a convenient and cost effective manner. However, under certain applications or tests it is advantageous that such membrane materials are not the same. For example, the membrane sampling device 34 can be used to test the performance of a new membrane material under conditions present in the field or at the site of use. Simply, an operator can obtain meaningful performance indicia under field conditions of different new membrane materials by using such new membrane materials in different cell-test membranes rather than by forming and inserting large, expensive membrane elements 18 into a particular filtration system. The performance indicia supplied by such new membrane materials can be used in designing optimal membrane elements for such applications.

Figure 3A:
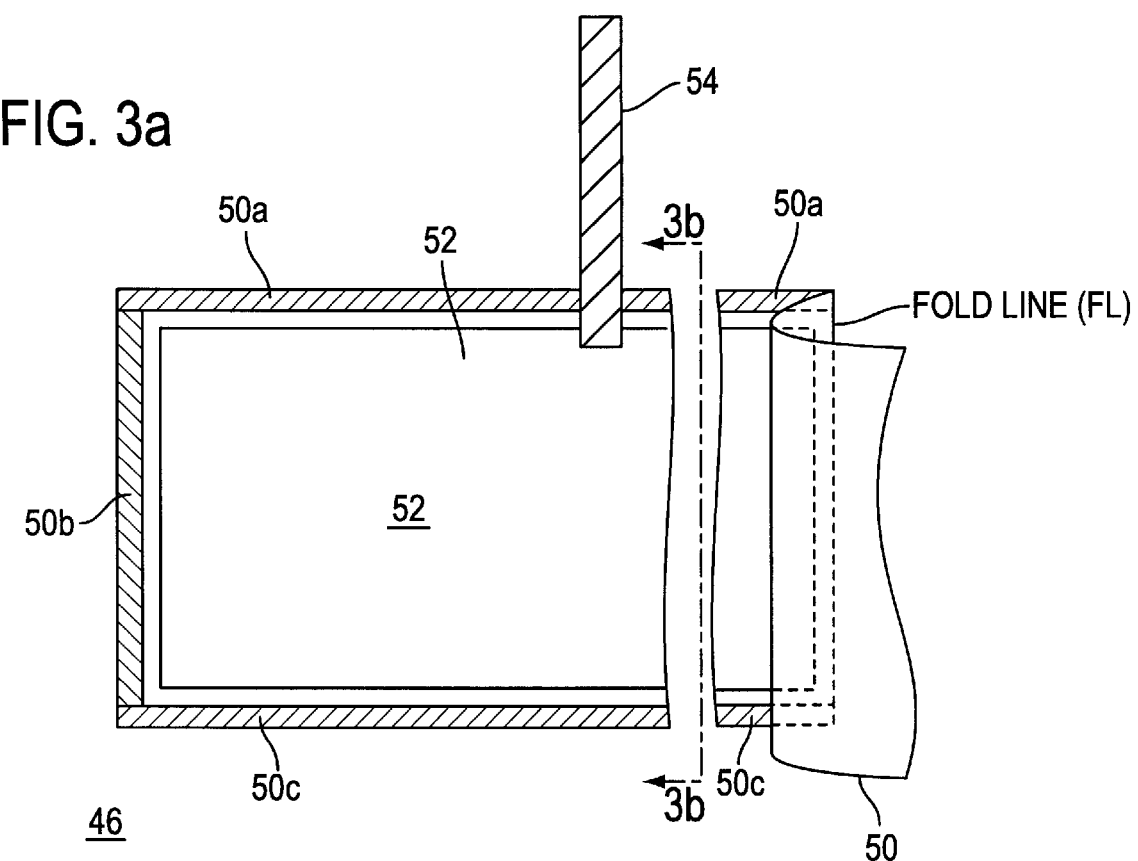
FIGS. 3a and 3b are schematic diagrams illustrating the membrane envelope of the membrane sampling device.
Figure 3B:
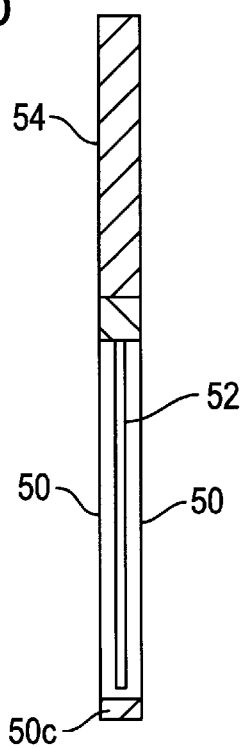

As is illustrated in FIGS. 3a and 3b, the cell-test membrane 46 includes an envelope 50, spacer material 52 and a small diameter tube 54. For example, the envelope 50 can be formed from one or more leaves of membrane material that are affixed at the outer edges 50a, 50b, and 50c. A rectangle of RO or UF membrane material of approximate size 5" long by 2" wide can be folded in the middle, along a fold line FT, thereby resulting in an envelope 2.5"×2" with one side closed. A feed spacer material 52 can be inserted into the formed membrane envelope 50, for example, a rectangle of spacer material 52 approximately 2.5"×2" is inserted into the membrane envelope formed by such folding. In addition, a small diameter plastic tube 54, for example, having a diameter of approximately 0.125", is inserted into the envelope 50 at one end, or in the middle, and the edges 50a, 50b and 50c are affixed using glue or other suitable adhesives. Later, after the adhesive has cured, the envelope can be rolled to form a cylinder having a diameter of approximately one inch resulting in the cell-test membrane 46 having one opening through tube 54. The adhesives used may be any glue or other adhesives suitable for the conditions in the pressure vessel and in the use of the membrane. The tube 54 can be made of any suitable material including plastics and the like whereby the materials can withstand the conditions of the pressure vessel.

After the glue has cured, which may take a few minutes to a few hours, the formed envelope has only one opening through the tube 54 so as to conduct permeate from the envelope 50. The tube 54 of the cell-test membrane 46 can be attached to the pipe 42, thereby the cell-test membrane 46 advantageously is removable from the end of the pipe 42 for easy replacement thereof. The perforated support holder or protective sleeve 48 can be placed around the cell-test membrane 46 having the tube 54 extending from the envelope 50 attached to the end of the central pipe 42 of the plug 38. In this manner, the cell-test membrane 46 can be formed and disposed in the pressure vessel 12 and advantageously can provide a convenient tool to monitor the membrane fouling and other conditions in RO/UF systems. Furthermore, the cell-test membrane has only a few square inches of membrane element material as compared to the larger membrane area of the membrane elements 18 disposed in the pressure vessel 12 and, as a result, the cell-test membrane of the present invention has the advantages of being small, compact and cost-efficient.

According to an embodiment of the present invention, and as will be appreciated by one skilled in the art, the membrane sampling device 34 can be sampled periodically under operating conditions for performance indicia of permeate flow and conductivity by removing the cap 44 to take samples of fluid from pipe 42. When necessary, the membrane sampling device 34 can be removed from the system 10 and replaced, whereby the operator turns off the flow and pressure to the particular pressure vessel, removes the plug 38 from the end plate 14 or the end plate 16, and inserts another device 34. In this manner, performance indicia indicative of the nature and degree of fouling of the membrane element 18 can be obtained without removing the end plates 14 or 16 from the system 10. The cell-test membrane 46 of a used membrane sampling device 34 can be analyzed on-site or can be sent to the manufacturer or other facility for testing. Each cell-test membrane 46 can further include a serial number or other coding so that individual cell-test membranes can be tracked, dated, evaluated and stored in compliance with any applicable governmental regulations or standard manufacturing operating procedures.

The advantages of the membrane sampling device 34 include providing performance indicia for the operation of the system 10 and the membrane element 18. A detailed analysis of the membrane surface can determine various things including the nature of any foulants. For example, during operation of RO systems, membrane material is exposed to the high pressure of the feed water. Exposure of the membrane elements to high pressure results in compaction, which will decrease the rate of diffusion of water and dissolved constituents through the membrane. As a result of such compaction, higher pressure has to be applied to maintain a desired permeate flow. Also, compaction causes a lower rate of salt diffusion resulting in lower permeate salinity. The effect of compaction is more significant in asymmetric cellulose membranes than in composite polyamide membranes. In seawater RO, feed pressure is significantly higher than in brackish applications, and results in greater compaction. Similarly, higher feed water temperature also will result in a higher compaction rate. Usually membrane compaction results in few percent flux decline, and has its strongest effect during the initial operating period. In the initial stages of membrane fouling, performance changes are similar to those caused by the compaction process. The fouling process is usually associated with an increase in pressure drop. An uncontrolled fouling process may lead to very severe performance degradation and even to complete destruction of membrane elements. The most effective way to control membrane fouling is to identify the origin of the fouling process early and eliminate it by the modifying pretreatment process or operating conditions. Foulant deposits can be removed from the membrane surface by chemical cleaning. However, success of the cleaning procedure depends on the age of the foulant deposit, and on proper selection of the cleaning solution.

The feed water, depending on its source, may contain various concentrations of suspended solids and dissolved matter. Suspended solids may consist of inorganic particles, colloids and biological debris such as microorganisms and algae. Dissolved matter may consist of highly soluble salts, such as chlorides, and sparingly soluble salts, such as carbonates, sulfates, and silica. During the RO process, due to removal of permeate, the volume of feed water decreases along the RO unit, and the concentration of suspended particles and dissolved ions increases. Suspended particles may settle on the membrane surface, thus blocking feed channels and increasing friction losses (pressure drop) across the system. Sparingly soluble salts may precipitate from the concentrate stream, create scale on the membrane surface, and result in lower fluid permeability through the RO membranes or flux decline. This process of formation of a deposited layer on a membrane surface is called membrane fouling and results in performance decline of the RO system. The objective of the feed water pretreatment process is to improve the quality of the feed water to the level that would result in reliable operation of the RO membranes. The quality of the feed water is defined in terms of concentration of suspended particles and saturation levels of the sparingly soluble salts. The common indicators of suspended particles used in the RO industry are turbidity and the Silt Density Index (SDI). The maximum limits specified by majority of membrane manufacturers are turbidity of 1 NTU and SDI of 4–5. Continuous operation of an RO system with feed water which has turbidity or SDI values at or near the limit levels may result in a significant membrane fouling. For long-term, reliable operation of the RO unit, the average values of turbidity and SDI in the feed fluid should not exceed 0.5 NTU and/or 2.5 SDI units, respectively. The indicators of saturation levels of sparingly soluble salts in the concentrate fluid stream are the Langlier Saturation Index (LSI) and the saturation ratios. The LSI provides an indication of the calcium carbonate saturation. Negative values of LSI indicate that the water is aggressive and that it will have a tendency to dissolve calcium carbonate. Positive values of LSI indicate the possibility of calcium carbonate precipitation. The LSI was originally developed by Langelier for potable water of a low salinity. For high salinity water encountered in RO applications, the LSI is an approximate indicator only. The saturation ratio is the ratio of the product of the actual concentration of ions in the concentrate stream to the theoretical solubility of the salts at predetermined conditions of temperature and ionic strength. These ratios are applicable mainly to sparingly soluble sulfates of calcium, barium and strontium. Silica could be also a potential scale forming constituent. Other potential scale forming salts are calcium fluoride or phosphate that may be present in RO feed. However, such salts seldom represent a problem and, once identified, a suitable cleaning procedure can be defined or crafted for a particular membrane filtration application. In this manner, the membrane sampling device 34 can enable convenient monitoring of the condition of the membrane element 18 operating in filtration systems including RO/UF filtration systems.

It is to be appreciated by one skilled in the art that the membrane sampling device 34 of the present invention advantageously is exposed to all the operating conditions, foulants and other particulate contaminants as the larger membrane element 18 disposed in the pressure vessel 12 of the membrane filtration system 10. Performance degradation under operating conditions can be determined by the use and analysis of the membrane sampling device 34 that has resided inside the pressure vessel during the operation of the RO/UF filtration system. The simplified testing apparatus and procedure contemplated by the present invention advantageously can be utilized to determine indices of performance without expensive examination of the membrane surface of the membrane element 18. Such performance determination can be correlated from an analysis of the smaller envelope 50 of the membrane sampling device 34 to the membrane element 18 operating in the pressure vessel 12 in a known manner. For example, the membrane sampling device 34 can easily be removed from the pressure vessel end plate 14 and 16, whereby the envelope 50 of the cell-test membrane 46 can be viewed under a microscope so as to evaluate the condition of the membrane surface. The membrane sampling device 34 can provide indicia of the fouling layer and test effectiveness of procedures and applications of membrane cleaning solutions as these are used in the commercial system. The ease of removal or replacement of the membrane sampling device 34 allows the operator not to severely disrupt the normal operation of the RO/UF filtration system beyond a very short time required to remove the plug 38 (or the cell-test membrane 46) and replace it. During the time that the plug 38 is removed, the pressure to such pressure vessel is shut off without removal of the end plate 14 or 16 and/or the membrane element 18. In this manner, the membrane sampling device 34 of the present invention advantageously reduces the considerable costs, down time and replacement and testing of otherwise expensive membrane or membrane elements.

Figure 5:
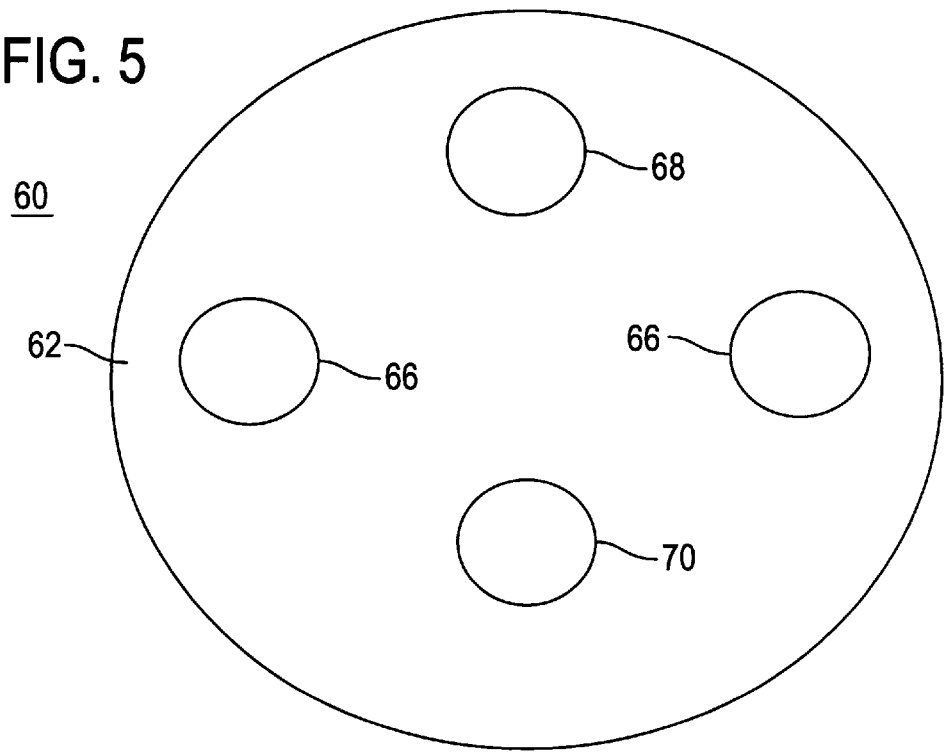
FIG. 5 is a top view of a modified plate for testing multiple membrane sampling devices.

As is illustrated in FIGS. 4 and 5, a testing system for the membrane sampling device 34 is illustrated according to an embodiment of the present invention. The testing system 60 includes a cover 62 adapted to fit on a testing tank 64. The cover 62 has one or more apertures 66 configured to receive one or more membrane sampling devices 34 for testing by the testing system 60. A feed aperture 68 and a concentrate aperture 70 are provided and configured to receive a supply of feed fluid and to collect concentrate fluid supplied to the pressure tank 64 in a known manner for testing of each membrane sampling device 34. As a result, individual membrane sampling devices 34 can be placed into apertures 66 for testing under normal or failure conditions prior to sale and insertion into the end plate 14 or 16 of pressure vessel.

Accordingly, the membrane sampling device of the present invention advantageously can identify many performance indicia as is set forth herein including membrane fouling. The membrane sampling device of the present invention can provide indicia or other information on the performance of individual membrane elements and such information is not readily available in current membrane filtration systems. The membrane sampling device of the present invention overcomes these and other shortcomings of the prior art to provide information on the performance of the filtration system in an effective and convenient way. For example, the present invention provides an improved method and apparatus for determining indicia of performance of a membrane element at the site of use whereby such information is advantageous, for example, to assess the degradation of the membrane element, to estimate the degree of fouling of the surface of the membrane element, to identify and design optimal membrane elements for specific field conditions, and to identify the nature and source of the foulant so as to determine an effective membrane cleaning procedure or solution. The present invention provides real-time performance indicia representative of the operating conditions in a pressure vessel having multiple membrane elements disposed therein. The membrane sampling device allows for the collection of performance indicia representative of the flux and conductivity of the feed, concentrate and permeate fluids in the membrane filtration system. Performance indicia can be obtained in real-time such as during the operation of the membrane filtration system, or with minimal interruption of the operation of the membrane filtration system. Such cell-test membrane provides performance indicia without the need to pack and unpack the membrane elements from the system.

The present invention also advantageously provides a cell-test membrane that gives performance indicia of the nature and degree of fouling of the membrane element and surface thereof in a small and compact cell-test membrane. The present invention provides an end plate having a separate aperture that provides a simple means to insert and remove the membrane sampling device from the pressure vessel and to allow for the collection of performance indicia respective of the flux and conductivity of the feed, concentrate and permeate fluids in the membrane filtration system. Such aperture also allows for the real-time testing of the conditions and performance indicia regarding the degree of fouling of the membrane elements in the pressure vessel using the cell-test membrane. Such aperture has advantages over prior devices that include minimizing the cost, downtime and conditions necessary to determine performance indicia of a particular membrane filtration system.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A device for providing performance indicia of a membrane filtration system, the device comprising:
   a plug having an opening, said plug adapted to be disposed in an end plate configured to seal an open end of a pressure vessel and said end plate including an aperture adapted to receive said plug, whereby said plug is configured to be received in said aperture, wherein said end plate includes a permeate port;
   a tube configured to be received by said opening; and
   a cell-test membrane disposed on said tube, said cell-test membrane located in said pressure vessel for effective sampling of performance indicia of the membrane filtration system.

2. The device of claim 1 wherein said opening is configured to receive a pipe along the length thereof, whereby said tube is adapted to be received by said pipe.

3. The device of claim 2 wherein said pipe is configured with an outer dimension less than an inner dimension of said tube so as to be received by said tube.

4. The device of claim 3 wherein said plug includes a closing cup for sealing said pipe during operation of the pressure vessel.

5. The device of claim 4 wherein said cell-test membrane is formed from an envelope, said envelope is comprised of a polyamide membrane material folded at a midpoint thereof, said envelope being affixed at the free edges formed by said midpoint to form said envelope.

6. The device of claim 1 wherein the performance indicia includes the nature and degree of foulant in the membrane filtration system.

7. The device of claim 1 wherein the performance indicia includes a permeate flow rate and composition of permeate collected from said cell-test membrane.

8. The device of claim 1 wherein said end plate includes a port for either feed or concentrate fluids.

9. The device of claim 1 wherein the pressure vessel includes ports for feed and concentrate fluids.

10. The device of claim 1 wherein said cell-test membrane is formed from an envelope, said envelope includes a membrane material and a spacer material, whereby said envelope is spirally-wound to form said cell-test membrane.

11. The device of claim 1 wherein said cell-test membrane is formed of material that is the same as the membrane material of a membrane element disposed in the membrane filtration system.

12. The device of claim 1 wherein said cell-test membrane is formed of material different than the membrane material of a membrane element disposed in the membrane filtration system.

13. The device of claim 1 wherein said cell-test membrane is formed from materials including cellulose acetate, polyamide, polysulfone, polypropylene and composite aromatic polyamide.

14. A device for determining the performance indicia for a membrane filtration system having a pressure vessel and an end plate configured to seat an open end of the pressure vessel, the device comprising:

a plug having an opening, said plug configured so as to be received in an aperture of the end plate, wherein said end plate includes a permeate port;

a tube configured to be received by said opening of said plug; and a cell-test membrane disposed on said tube, said cell-test membrane located in said pressure vessel for effective sampling of performance indicia of the membrane filtration system.

15. The device of claim 14 wherein said plug has an outer dimension less than an inner dimension of said aperture formed in the end plate.

16. The device of claim 15 wherein the performance indicia includes the nature and degree of foulant in the membrane filtration system.

17. The device of claim 16 wherein the performance indicia includes a permeate flow rate and composition of permeate collected from said cell-test membrane.

18. The device of claim 17 wherein said plug includes a closing cup for sealing the opening during operation of the pressure vessel, said closing cup adapted to withstand the operating pressure of the pressure vessel.

19. The device of claim 18 wherein said cell-test membrane is formed from an envelope, said envelope is comprised of a polyamide membrane material folded at a midpoint thereof, said envelope being affixed at the free edges formed by said midpoint to form said envelope.

20. The device of claim 19 wherein said cell-test membrane can be removed from the membrane filtration system and evaluated for performance indicia.

21. The device of claim 20 wherein said cell-test membrane can be removed from the membrane filtration system and can be evaluated for the nature and degree of foulant in the membrane filtration system.

22. The device of claim 21 wherein said cell-test membrane can be removed from the membrane filtration system and can be evaluated for effectiveness of membrane cleaning procedures.

23. An end plate for use in a pressure vessel of a membrane filtration system, the end plate configured to seal an open end of a pressure vessel, the end plate comprising:

an aperture formed in the end plate; and a membrane sampling device adapted to be received in said aperture, said membrane sampling device being configured to determine performance indicia of a membrane element disposed in the pressure vessel and other conditions of the membrane filtration system, wherein said end plate includes a permeate port.

24. The end plate of claim 23 wherein said membrane sampling device includes:

a plug having an opening, said plug being configured with an outer dimension less than an inner dimension of said aperture so as to be received in said aperture;

a tube configured to be received by said opening of said plug; and a cell-test membrane disposed on said tube, said cell-test membrane located in said pressure vessel for effective sampling of performance indicia of the membrane filtration system.

25. The end plate of claim 24 wherein said cell-test membrane includes an envelope formed of a membrane material and a spacer material, whereby said envelope is spirally-wound to form said cell-test membrane.

* * * * *